United States Patent [19]
Hijikihigawa et al.

[11] Patent Number: 5,140,393
[45] Date of Patent: Aug. 18, 1992

[54] SENSOR DEVICE

[75] Inventors: Masaya Hijikihigawa, Yamatokoriyama; Shoei Kataoka, Tanashi, both of Japan

[73] Assignee: Sharp Kabushiki Kaisha, Osaka, Japan

[21] Appl. No.: 579,195

[22] Filed: Sep. 5, 1990

Related U.S. Application Data

[63] Continuation of Ser. No. 284,773, Dec. 12, 1988, abandoned, which is a continuation of Ser. No. 914,808, Oct. 3, 1986, abandoned.

[30] Foreign Application Priority Data

Oct. 8, 1985 [JP] Japan .................. 60-225439

[51] Int. Cl.⁵ ..................... H01L 29/66; H01L 29/96
[52] U.S. Cl. .................. 357/25; 357/23.15; 204/403; 204/412
[58] Field of Search ............ 357/25, 23.15; 204/403, 204/409, 412, 416

[56] References Cited

U.S. PATENT DOCUMENTS

| | | | |
|---|---|---|---|
| 4,020,830 | 5/1977 | Johnson et al. | 357/25 |
| 4,218,298 | 8/1980 | Shimada et al. | 357/25 |
| 4,411,741 | 10/1983 | Janata | 357/25 |
| 4,486,292 | 12/1984 | Blackburn | 357/25 |
| 4,490,216 | 12/1984 | McConnell | 357/25 |
| 4,644,380 | 2/1987 | Zemel | 357/25 |

FOREIGN PATENT DOCUMENTS

| | | | |
|---|---|---|---|
| 2947050 | 5/1981 | Fed. Rep. of Germany | 357/25 |
| 59-61063 | 4/1984 | Japan | 357/23.1 |
| 2029583A | 8/1979 | United Kingdom | 357/25 |

OTHER PUBLICATIONS

"The Impact of Mosfet-Based Sensors", by P. Bergveld Presented at the Third International Conference of Solid-State Sensors and Actuators (Transducers '85), Philadelphia, Pa., Jun. 11–14, 1985.

Primary Examiner—Andrew J. James
Assistant Examiner—Sara W. Crane
Attorney, Agent, or Firm—Bryan Cave

[57] ABSTRACT

A sensor device comprising a substrate and a sensor formed on thereof which is made of a metal, metallic oxide, semiconductor, dielectric or organic material, the sensor having projections or indentations formed on or in its surface with optional predetermined shape and dimensions; which is useful as a chemical sensor, biosensor or physical sensor device of improved performance and function.

10 Claims, 5 Drawing Sheets

SENSOR DEVICE

This application is a continuation of application Ser. No. 284,773, filed Dec. 12, 1988 abandoned which in turn is a continuation of application Ser. No. 914,808, filed Oct. 3, 1986, abandoned.

BACKGROUND OF THE INVENTION

1. Field of the Invention

The present invention relates to the structure of a sensor which undergoes a chemical or physical interaction with the object (amount) to be detected and which is adapted for use in chemical sensor devices for detecting chemical amounts of gases, humidity, ions, etc., biosensor devices for detecting physiologically active substances such as uric acid and glucose, or physical sensor devices for detecting physical quantities of electromagnetic waves, temperature, etc. More particularly, the invention relates to the structure of a sensor which has a surface shaped to a suitably predetermined optimum form by an artificial reproducible method such as a fine processing technique so as to exhibit improved performance.

The sensors embodying the present invention are not always limited to those acting to convert the object (amount) to be detected directly to an electric signal but also include those performing an indirect converting action, for example, by undergoing chemical or physical interaction with the object (amount) to convert the same to another chemical or physical quantity.

2. Description of the Prior Art

Gas sensor devices are adapted to detect a specified component gas of a gaseous mixture in terms of an electric signal, for example, by (1) utilizing a phenomenon on the solid surface of a sensor resulting from the adsorption of the gas by the surface, (2) utilizing the reactivity of a sensor with the gas,

(3) utilizing concentration polarization (electromotive force) due to a solid electrolyte, or (4) utilizing the physical properties (thermal conductivity, infrared absorption, etc.) of molecules of the gas.

Figure 7:
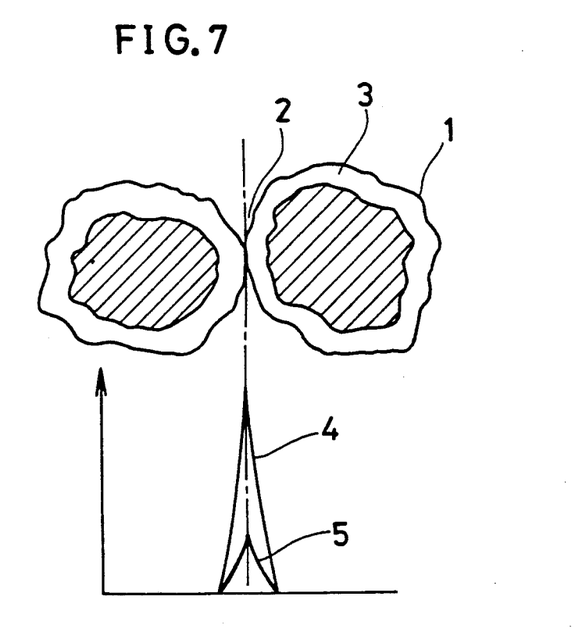
FIG. 7 is a diagram for illustrating the detection mechanism of a conventional semiconductor gas sensor.

Generally, semiconductor gas sensor devices are based on the principle that when gas molecules (or radicals) are adsorbed by the surface of an n-type or p-type semiconductor (sensor) composed chiefly of a metallic oxide such as tin oxide ($SnO_2$), zinc oxide (ZnO), nickel oxide (NiO) or cobalt oxide (CoO), transfer of electrons or uneven presence of charges occurs between the semiconductor and the adsorbed molecules (radicals) to form a space-charge layer in the vicinity of the semiconductor surface, consequently varying the electrical conductivity of the semiconductor, the variation in the conductivity thus indicating the presence of the gas. For example, when a semiconductor of $SnO_2$, ZnO or like metallic oxide exhibiting n-type conductivity adsorbs a combustible gas such as hydrogen, carbon monoxide or hydrocarbon, transfer of charges between the adsorbed gas molecules and the semiconductor (donation of electrons by the adsorbed gas molecules) gives increased electrical conductivity in the vicinity of the semiconductor surface. Thus, the variation in the electrical conductivity due to the adsorption of the gas is detectable as a variation in the surface electrical conductivity. This means that if the surface of the sensor is increased relative to its volume, for example, by reducing the thickness thereof, the variation ratio of the conductivity increases to render the sensor serviceable advantageously. However, many of actual semiconductor gas sensors are polycrystalline bodies obtained by sintering a powder and have in the body of the sensor a contact portion or neck portion between crystal grains. For example when there is a boundary 2 between crystal grains 1 in contact with each other as shown in FIG. 7, a space-charge layer 3 is formed over the surface of the grains exposed to the atmosphere, owing to the influence of adsorbed oxygen (electron acceptor), so that the two grains contact each other through the space-charge layer 3. Accordingly, an electron barrier indicated in a curve 4 is formed between the grains to impede the movement of electrons between the grains. It is thought that when a combustible gas comes into contact with the grains, the adsorbed oxygen is consumed or removed by combustion, lowering the potential barrier as indicated in a curve 5 in FIG. 7 and increasing the electrical conductivity. With the actual semiconductor gas sensor, the contact portion at the grain boundary contributes a great deal to the gas detecting mechanism, permitting the sensor to exhibit pronounced variations in the surface electrical conductivity. On the other hand, the output characteristics, i.e. the conductivity-gas concentration characteristics, of the semiconductor gas sensor are dependent on alterations in the minute structure of the contact portion or neck portion between the crystal grains. This is a great factor causing the characteristics to differ from sensor to sensor. Basically, therefore, it is necessary to control the size and shape of the grains and the state of fusion between the grains with good reproducibility. From the viewpoint of sensitivity to gas, it is also necessary to increase the area of adsorption of gas so that the space-charge layer formed in the vicinity of the sensor surface will greatly contribute to the conductivity as already described.

When sensors are to be prepared by a conventional method, for example, by sintering a powder, the sintering temperature and time, addition of the sintering agent, gaseous sintering atmosphere, etc. are controlled empirically by relatively controlling indirect conditions. Nevertheless, when such indirect condition control is resorted to, it is not always possible to control a single factor only. For example, depending on the sintering time or temperature, at least the size and shape of the crystal grains vary, and the state of fusion between the grains (state of the grains bound together) also alters. For this reason, it is extremely difficult to produce with good reproducibility sensors which are identical in structure when viewed on a microscale.

Next, conventional biosensor devices will be described. Generally, biosensor devices comprise a sensor called a receptor which is prepared by fixing a living body associated substance, such as an enzyme, antibody or organella of the living body, to a suitable substrate (film), and a transducer for converting to an electric signal a gas or like chemical substance or physical amount of light, heat or the like resulting from, or eliminated by, the reaction of the receptor with the substance to be detected. For example, in the case of sensor devices for detecting glucose, the receptor is prepared by fixing an enzyme (glucose oxidase, GOD) to a high polymer film. When glucose contacts the enzyme GOD, hydrogen peroxide ($H_2O_2$) is formed according to the following reaction formula.

The H₂O₂ produced is detected in terms of an electric signal using electrochemical means (transducer) having, for example, a platinum anode. Thus, the concentration of the substance to be detected, i.e. glucose, can be determined by detecting the amount of the resulting $H_2O_2$. While the chemical substance produced is detected by the transducer in this way, methods are also known of detecting emission of light or endothermic, exothermic or like thermal phenomenon resulting from the reaction between the enzyme and the substance to be detected. When the light emitting phenomenon is utilized, a photodetector is used as a transducer, while a thermistor or like temperature sensor is used for detecting the thermal phenomenon. In any case, the lower limit of the detectable concentration of the object substance is almost always dependent on the amount of reaction between the receptor and the substance. Accordingly, the sensitivity of detection is increased by fixing the living body associated substance, such as enzyme, with the highest possible density, or by increasing the area of contact of the receptor with the substance to be detected. However, the increase in the area of the receptor is physically limited because the enzyme or the like is fixed usually to a flat substrate and further because the size of the receptor needs to be considered relative to the size of the transducer.

Next, temperature sensors heretofore known will be described. Temperature sensors generally include those adapted to detect infrared rays, those utilizing the variation of electrical resistance with temperature and those utilizing thermal electromotive force. So-called thin film temperature sensors will be described below in which the temperature measuring element is a thin film of platinum, nickel or like material having a great temperature coefficient of resistance.

The temperature measuring elements for thin film temperature sensors must fulfill the requirements of having a great temperature coefficient of resistance which is constant over a wide temperature range, being low in resistance value at a reference temperature (e.g. 0° C. or 100° C.) so as to be interchangeable, having a resistance value in a readily usable range for temperature measurement (e.g. a resistance value $R_0$ of 100 Ω or 1 kΩ at 0° C.), being small, etc. Accordingly, the conventional temperature measuring element is produced by forming a thin film of platinum, nickel or like metal having a high purity on a substrate of ceramics or the like having a surface made planar to the greatest possible extent, by vacuum evaporation or sputtering, and thereafter forming the film into a pattern of lines having a specified width by photoetching or other technique. To give the temperature measuring element a minimized area and a resistance value $R_0$ which is convenient to use, e.g. 100 Ω or 1 kΩ, at a reference temperature (e.g. 0° C.), the pattern is prepared in a zigzag (meandering) form with a minimized line width. However, because of the limitations actually involved in the processing technique especially when platinum is used, it is difficult to obtain a pattern up to several micrometers in line width and line spacing, consequently imposing limitations on minimizing the size of the temperature measuring element. With temperature measuring elements having a resistance value $R_0$ of 1 kΩ, the lower limit of the size of elements is approximately 1 to 2 mm square.

SUMMARY OF THE INVENTION

The present invention provides a sensor device comprising a substrate and a sensor formed thereon which is made of a metal, metallic oxide, semiconductor, dielectric or organic material and provided at least on the surface thereof with a plurality of projections having optimal predetermined shape and dimensions.

BRIEF DESCRIPTION OF THE DRAWINGS

FIGS. 1 (a) to (g) are fragmentary perspective views schematically showing sensors embodying the present invention;

DESCRIPTION OF THE PREFERRED EMBODIMENTS

The above-mentioned projections (indentations) are formed on the surface of a substrate by chemical or physical finely processing means or on the surface of the sensor by chemical or physical finely processing means. Alternatively, the projections are formed by selective film forming means or selective crystal growing means when the sensor is prepared. The projections are intended to provide a sensor having an optimum shape with respect to the sensing characteristics to exhibit improved performance. The present invention further assures good reproducibility in preparing sensors and therefore makes it possible to produce sensors in quantities with uniform operating characteristics.

Application to semiconductor gas sensor devices

The present invention will be described with reference to semiconductor gas sensor devices which utilize the alteration of a phenomenon on the surface of a solid due to the adsorption (desorption) of gas, especially variations in the electrical conductivity of a semiconductor sensor.

FIG. 1 (a) is a perspective view showing a sensor for semiconductor gas sensor devices. A tin oxide film is selectively formed on the surface of an insulating substrate 11 of glass, ceramics or the like by RF sputtering, vacuum evaporation or crystal growth, whereby projections (or indentations) are formed on the surface of the tin oxide film. Alternatively, a uniform tin oxide film is formed over the surface of the substrate 11 by RF sputtering or vacuum evaporation and is thereafter finely processed into a wavelike form as illustrated by photolithography and a dry etching process such as chemical etching or plasma etching. Instead of finely processing the tin oxide film, the surface of the substrate 11 may be sandblasted to form fine trapezoidal projections 13 thereon, followed by the deposition of tin oxide on the surface of the projections 13 to form a sensitive film 12 having projections or indentations. These three fine processing methods may be practiced at least twice repeatedly. The shape of the projections need not always be trapezoidal as illustrated in FIG. 1 (a) but can be pyramidal, conical or semispherical. For example, FIG. 1 (b) shows rectangular projections, FIG. 1 (c) trapezoidal projections formed by anisotropic etching, FIG. 1 (d) overhanging projections formed by anisotropic etching, FIG. 1 (e) projections in a meshlike arrangement, and FIG. 1 (f) indentations in a meshlike arrangement. Further as seen in FIG. 1 (g), projections or indentations are formed only at the outer peripheral portion of the substrate 11 to prevent peeling of the sensitive film.

The projections or indentations may be arranged periodically or otherwise. The shapes of projections or indentations shown in FIGS. 1 (a) to (f) are also usable for the following embodiments.

With reference to FIG. 1 (a), the distance d between the substrate 11 and the bottom surface 14 of the indentation formed in the tin oxide sensitive film 12 by fine processing is preferably as large as the thickness (Debye length) of the space-charge layer. Because the Debye length varies with the energy position and density of the tin oxide at the surface level thereof, the distance d can not be determined specifically, but the optimum value thereof can usually be in the range of from 0.1 to several micrometers. An improved detection sensitivity can be obtained when an element having a catalytic action, such as platinum or palladium, is added to the film forming material when the tin oxide sensitive film is to be formed.

When the sensor adsorbs a combustible gas, the potential barrier lowers as shown in the curve 5 in FIG. 7 to result in increased electrical conductivity.

The gas sensors having a finely processed surface as described above have the following advantages over the conventional gas sensors.

Figure 1A:
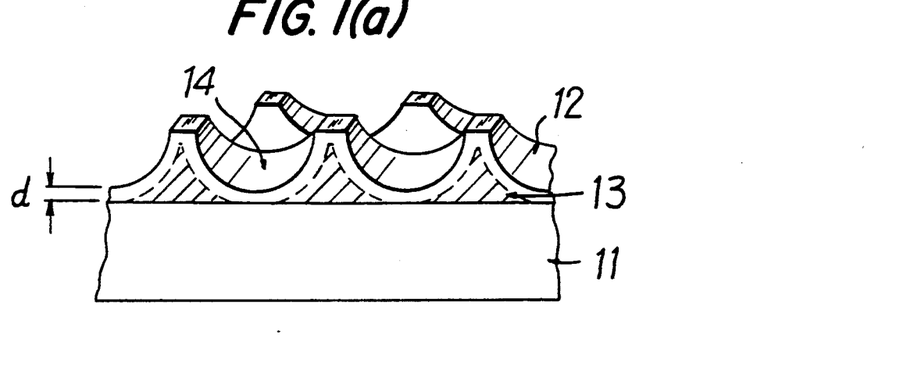
Figure 1B:
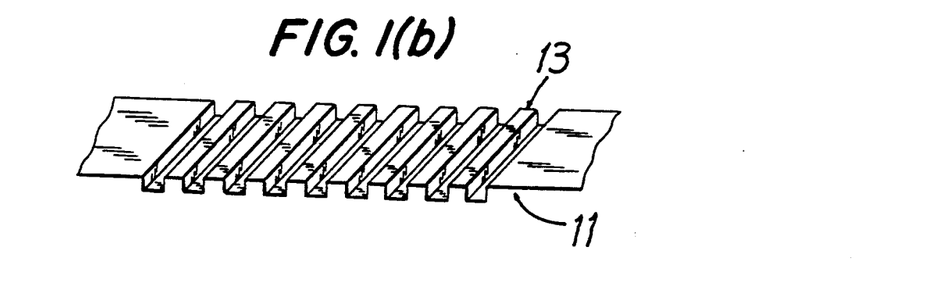
Figure 1C:
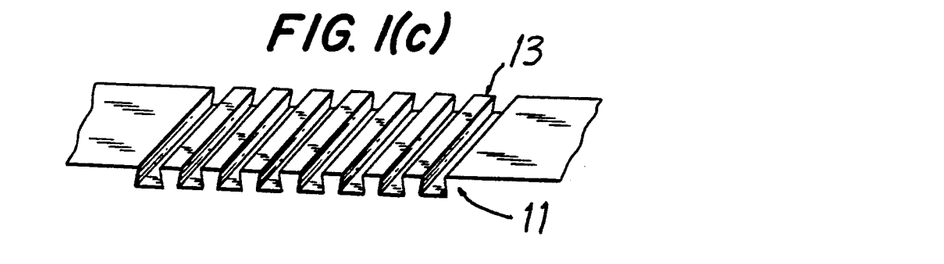
Figure 1D:
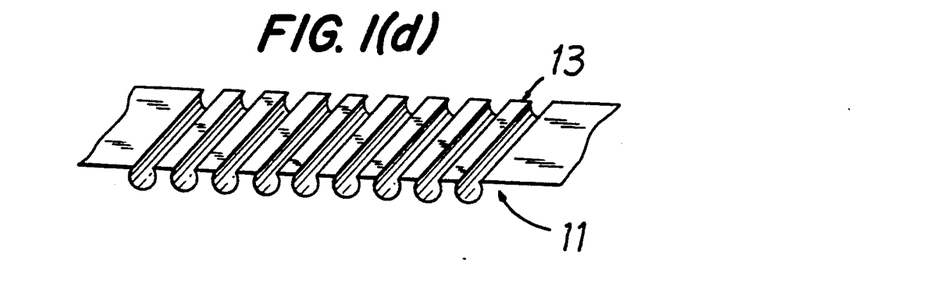
Figure 1E:
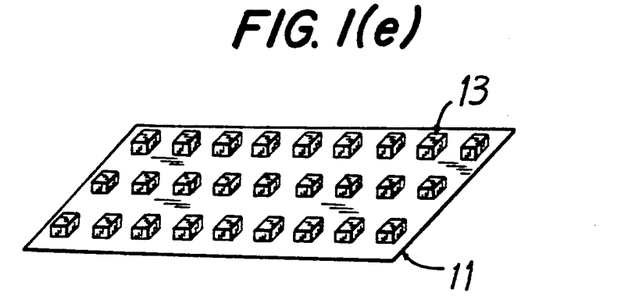
Figure 1F:
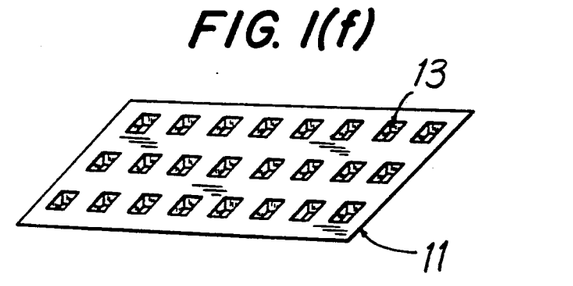
Figure 1G:
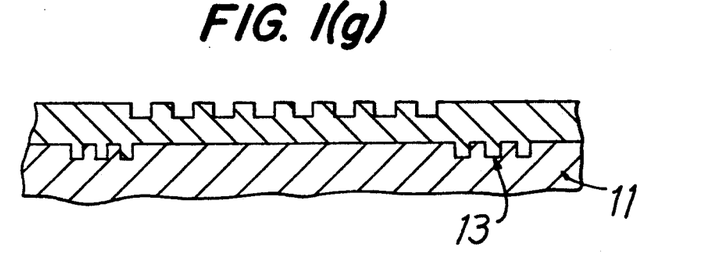

(1) The contact portion or neck portion between the crystal grains in the conventional gas sensor made of a sintered body corresponds to the distance between the substrate 11 and the bottom surface 14 of indentations of the present sensor, so that gas detecting characteristics can be obtained with good reproducibility by directly controlling the distance d by fine processing.

(2) The pitch of the finely processed projections or indentations corresponds to the crystal grain of the conventional sintered body, and the projections or indentations can be suitably sized so as to have the specified shape and dimensions. Consequently, the result achieved is equivalent to that obtained when the crystals have a uniform distribution in a plane. The gas detecting characteristics are controllable intentionally, while the desired characteristics are available with good reproducibility (with diminished variations).

(3) With an increased surface area given to the sensor per unit area of the substrate, the sensor has an increased area for adsorbing a gas, exhibiting an enhanced gas detection sensitivity, i.e. improved detecting characteristics.

(4) Since the dependence of the electrical conductivity not only on the concentration of gas but also on the kind of gas can be altered by varying the distance d, satisfactory gas selectivity is available.

Not only tin oxide but also zinc oxide, nickel oxide, cobalt oxide and like semiconductors of n-type or p-type are similarly usable for forming the gas sensor. From the viewpoint of finely processing techniques, however, it is desirable to use a single crystal, aggregate of fine crystals or amorphous material.

EXAMPLE 1

Figure 2:
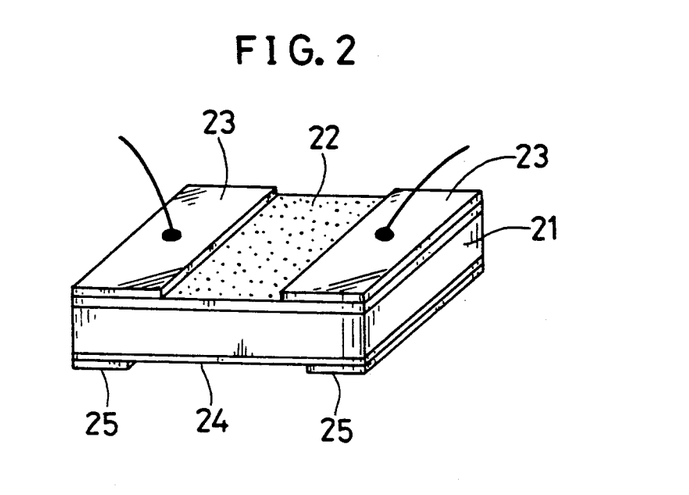
FIG. 2 is a persective view schematically showing a semiconductor sensor device incorporating one of the sensors shown in FIGS. 1 (a) to (g)

FIG. 2 is a diagram showing a semiconductor gas sensor device incorporating the above sensor.

A tin oxide film, is formed on the upper surface of a ceramics substrate 21 by RF sputtering, and the surface of the tin oxide film is finely processed by photolithography and chemical etching. Platinum electrodes 23 are thereafter formed on the film at its opposite ends for measuring the electrical conductivity of the resulting sensor 22. A heater resistor 24 of platinum and electrodes 25 therefor are provided on the lower surface of the substrate for heating the sensor 22 during operation. Current is passed across the electrodes 25 to heat the resistor 24 and heat the sensor 22 to a suitable temperature. When the sensor 22 is placed in this state in a gas atmosphere, i.e. the object to be detected, the electrical resistance value of the sensor 22 varies with high sensitivity owing to the presence of the gas. The variation is detected via the opposed metal electrodes 23, whereby the presence of the gas is detectable.

Application to biosensor devices

The present invention will be described next with reference to semiconductor biosensor devices for detecting a substance based on a reaction between the substance and a receptor (sensor) comprising an enzyme or other living body associated substance.

Figure 3:
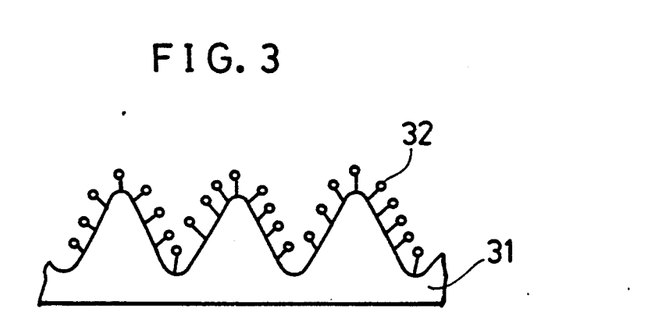
FIGS. 3 and 4 are fragmentary diagrams for illustrating other embodiments of the present invention.

FIG. 3 is a fragmentary diagram showing a sensor for this purpose. Minute projections (indentations) arranged periodically or randomly as illustrated are formed at least on the surface of a substrate 31 of organic high polymer material such as polyvinyl alcohol (PVA) cellulose ester, for example, by chemical etching or plasma etching. Subsequently, a living body associated substance 32 such as glucose oxidase, invertase, mutarotase, galactose oxidase, amino acid oxidase, urease, uricase or like enzyme or lactic acid bacterium, butyric acid bacterium, methane oxidizing bacterium or like microorganism is fixed to the finely processed substrate surface by the covalent bond method or adsorption method to obtain a receptor (sensor). When thus prepared, the receptor has a larger amount of living body associated substance fixed to the substrate per unit area thereof and a larger area of contact with the substance to be detected than the conventional flat-surfaced receptor (sensor). Consequently, the sensor is given a higher detection sensitivity or can be made smaller in its entirety than the conventional ones having the same sensitivity.

Figure 4:
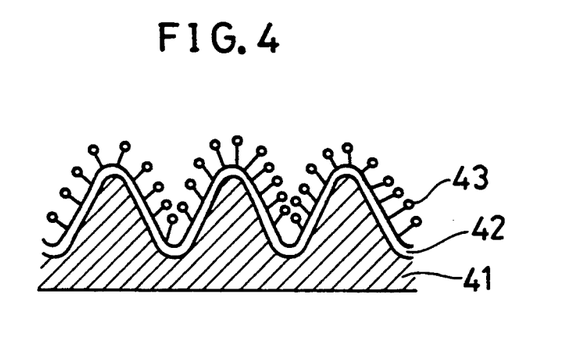

If it is impossible to fix the living body associated substance directly to the finely processed substrate surface or if it is difficult to finely process a substrate suited for fixing, a sensor of double layer structure as shown in FIG. 4 is usable as a receptor. With reference to the drawing, a substrate 41 is finely processed first, and a sensitive film 42 having fixed thereto the same living body associated substance 43 as mentioned above is formed on the substrate surface. The sensitive film 42 can be formed effectively on the substrate 41, for example, by Langmuir-Blodgett's technique. Further when a single crystal is usable as the substrate 41, the substrate can be finely processed utilizing the dependence of chemical etching speed on the orientation of crystal, i.e. by the anisotropic etching technique. When the sensor is physically coupled to an electrochemical device or a transducer such as a photodetector or temperature sensor to provide a sensor device of conventional construction, the device is serviceable as a biosensor device having a higher detection sensitivity than those heretofore known.

The biosensor device can be adapted to give an electric output with high sensitivity when provided on the channel region of a field-effect transistor (FET) directly or with a gate insulating film formed therebetween.

EXAMPLE 2

Figure 5:
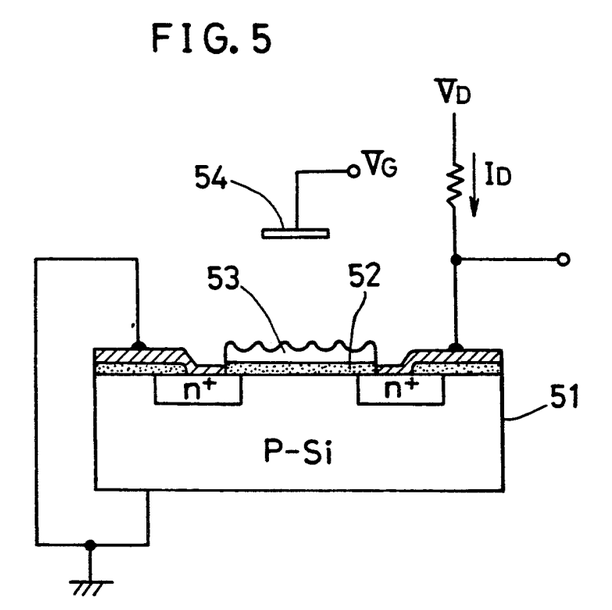
FIG. 5 is a diagram in section showing the sensor of the invention as incorporated in a field-effect transistor.

Two n+ regions spaced apart are formed in the surface of a p-type silicon substrate, and a gate insulating film 52 of silicon oxide ($SiO_2$) is formed over the substrate surface between the n+ regions. A polyvinyl alcohol layer is formed over the gate insulating film 52. Minute projections (indentations) are randomly formed on the surface of the polyvinyl alcohol layer by plasma etching. Glucose oxidase is fixed to the etched surface by adsorption to provide a sensor 53. A reference electrode 54 is opposed to the sensor 53 as spaced therefrom by such a distance as to permit the solution to be detected to pass therebetween. A predetermined potential is provided across the FET and the reference electrode 54 in the solution. The slight variation in the potential due to a reaction between the solution and the sensor is detected in terms of a variation in the gate current of the FET and is delivered as a greater variation in the drain current $I_D$ utilizing the amplification of the FET.

Thus, the sensor of the present embodiment is usable as electrically or physically connected to any kind of transducer heretofore known to provide a biosensor device of improved performance.

EXAMPLE 3

Application to thin film temperature sensor device

The invention will be described with reference to a thin film temperature sensor device wherein a thin film sensor of a material, such as platinum, having a great temperature coefficient of resistance is used as the temperature measuring element.

Figure 6:
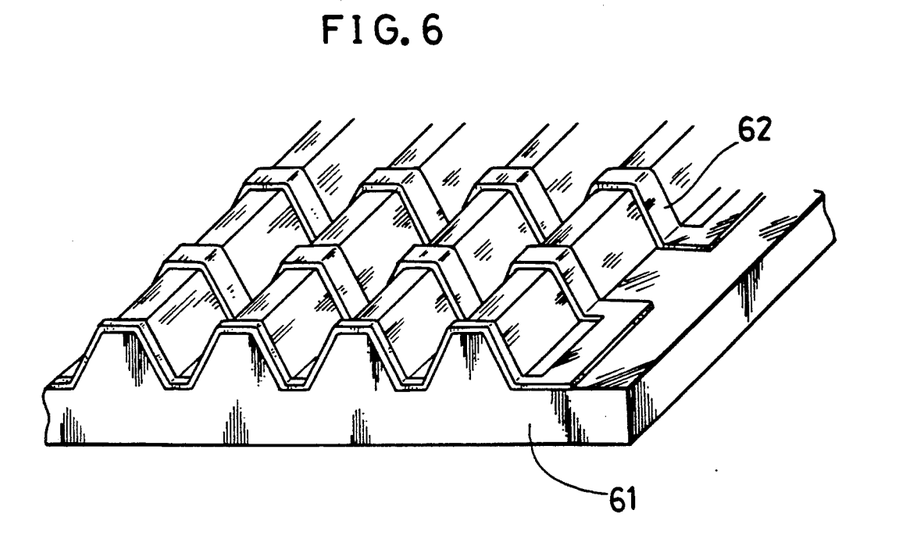
FIG. 6 is a fragmentary perspective view schematically showing a sensor for use in a thin film temperature sensor device for illustrating another embodiment of the invention.

FIG. 6 is a perspective view schematically showing the sensor device.

A substrate 61 having a sufficiently low specific resistance than platinum film, for example, a high-resistance silicon wafer, is finely processed by anisotropic etching at least over the surface thereof to the shape of flat-crested waves having a definite or indefinite period as illustrated, whereby trapezoidal projections or indentations are formed on or in the surface of the substrate 61. Subsequently, a platinum film 62 is formed over the etched surface of the substrate 61 by RF sputtering and is thereafter shaped into a pattern of zigzag lines of specified width and spacing by photoetching or sputter-etching. The platinum film 62 thus prepared serves as a temperature measuring element the resistance value of which varies with temperature. Since the resistance of the platinum film conductor 62 is greater than when the conventional flat substrate is used by an amount corresponding to the projections or indentations of the substrate surface, the temperature measuring element having a specified $R_0$ value can be exceedingly smaller than the corresponding conventional ones. Furthermore, platinum conductors which are identical in film thickness and line width can be given different reference resistance values by altering the processed shape of the substrate or the pitch of projections. The substrate need not always have high resistance but may be made to have a surface of increased resistance by being thermally oxidized after the fine processing or by being covered with an additional insulating film.

As described in detail above, the sensor device of the invention comprises a crystalline, fine crystalline or amorphous sensor made of a semiconductor, metal, metallic oxide, dielectric or organic material and having projections or indentations formed on or in its surface with optional predetermined shape and dimensions by a finely processing technique. Thus, the sensor is characterized by its surface shaped to exhibit intentionally controlled sensing characteristics. As will be apparent from the foregoing embodiments, the reaction or interaction between the substance (amount) to be detected and the sensor can be enhanced by increasing the surface area and utilizing the shape of the surface. Accordingly the present sensor is very useful in providing chemical sensor, biosensor or physical sensor devices of improved performance and function.

What is claimed is:

1. An improved semiconductor sensing device having a substrate having a surface, a channel region formed in said substrate surface, source and drain electrodes formed on said substrate for enabling an electric current to flow therebetween.

a reference electrode, opposed to and spaced from said channel region for applying a potential across said channel region and varying said electric current between said source and drain electrodes, and a sensor for a substance to be detected formed on said substrate surface over said channel region, said sensor being adapted to receive a fluid flow between said channel region and said reference electrode;

wherein the improvement comprises:

said sensor comprising a living body associated substance being fixed to said substrate surface over said channel region to form a plurality of configured projections of predetermined shape and pitch formed over said channel region, said projections causing said living body associated matter to have an enhanced area of contact with said fluid flow, said projection shapes and pitches being shaped according to a predetermined optimal sensing characteristic such that when said sensor detects said substance to be detected said potential across said channel region varies so that said electric current between said source and drain electrodes becomes a maximum;

wherein said enhanced area of contact caused by said projections providing an enhanced reproducible potential variation across said channel region over time, thereby providing an enhanced reproducible drain current through said channel region over time for said sensor, and thereby providing an enhanced detection sensitivity of said sensor over time.

2. An improved semiconductor sensing device in accordance with claim 1 wherein said predetermined shape comprises a shape at least selected from the group consisting of trapezoidal, pyramidal, conical, semispherical and rectangular.

3. An improved semiconductor sensing device in accordance with claim 1 wherein said pitch of said projections comprises a periodic arrangement of said projections.

4. An improved semiconductor sensing device in accordance with claim 1 wherein said projections are formed on said substrate at an outer peripheral portion of said substrate where said channel region is not formed, said projections preventing peeling of said sensor from said surface.

5. An improved semiconductor sensing device in accordance with claim 1 wherein said pitch of said projections comprises a random arrangement of sad projections.

6. An improved semiconductor device as defined in claim 1 wherein said sensor comprises a metal, metallic oxide, semiconductor, or dielectric.

7. An improved semiconductor device as defined in claim 1 wherein said sensor comprises an enzyme or a bacterium.

8. An improved semiconductor sensing device having a substrate having a surface,
a channel region formed on said substrate surface,
source and drain electrodes formed on said substrate for enabling an electric current to flow therebetween,
a sensor for detecting a substance, formed on the channel region, said sensor having a surface,
and a reference electrode opposed to and spaced from said channel region to enable a fluid flow between said channel region and said reference electrode;
wherein the improvement comprises:
said sensor surface comprising a living body associated substance and having a plurality of configured projections formed thereon,
said projections providing an enhanced area of contact with said fluid flow and providing an enhanced reproducible potential variation across said channel region over time, thereby providing an enhanced reproducible detection sensitivity of said sensor over time; whereby enhanced detection results may be obtained with good reproducibility.

9. An improved semiconductor sensing device in accordance with claim 8 wherein said projections are formed on the surface of the sensor by chemical or physical finely processing means.

10. An improved semiconductor sensing device having a substrate having a surface,
a channel region formed in said substrate surface,
source and drain electrodes formed on said substrate for enabling an electric current to flow therebetween,
a reference electrode opposed to and spaced from said channel region for applying a potential across said channel region and varying said electric current between said source and drain electrodes, and
a sensor for a substance to be detected formed on said substrate surface over said channel region, said sensor being adapted to receive a fluid flow between said channel region and said reference electrode;
wherein the improvement comprises:
said sensor comprising a living body associated substance film being fixed to and covering substantially all of said substrate surface over said channel region to form a plurality of configured projections of predetermined shape and pitch formed over said channel region, said projections causing said living body associated matter to have an enhanced area of contact with said fluid flow, said projection shapes and pitches being shaped according to a predetermined optimal sensing characteristic such that when said sensor detects said substance to be detected said potential across said channel region varies so that said electric current between said source and drain electrodes becomes a maximum;
wherein said enhanced area of contact caused by said projections providing an enhanced reproducible potential variation across said channel region over time, thereby providing an enhanced reproducible drain current through said channel region over time for said sensor, and thereby providing an enhanced detection sensitivity of said sensor over time.

* * * * *

UNITED STATES PATENT AND TRADEMARK OFFICE
CERTIFICATE OF CORRECTION

PATENT NO. : 5,140,393
DATED : August 18, 1992
INVENTOR(S) : MASAYA HIJIKIGAWA, et al It is certified that error appears in the above-identified patent and that said Letters Patent is hereby corrected as shown below:

On the title page: Item [75]

In Inventors: Delete "Hijikihigawa" and insert --Hijikigawa--.

Delete "Tanashi" and insert --Tokyo--.

Column 1, line 23: Delete "fine" and insert --finely--

Column 5, line 2: Delete "fine" and insert --finely--.

Column 9, line 11: Delete "sad" and insert --said--.

Column 9, line 26, After surface delete "," and insert --;--

Signed and Sealed this

Sixteenth Day of November, 1993

Attest:

BRUCE LEHMAN

Attesting Officer　　Commissioner of Patents and Trademarks